United States Patent
Ingram et al.

(10) Patent No.: US 9,314,770 B2
(45) Date of Patent: Apr. 19, 2016

(54) AUTOGENIC REACTION SYNTHESIS OF PHOTOCATALYSTS FOR SOLAR FUEL GENERATION

(75) Inventors: Brian J. Ingram, Chicago, IL (US); Vilas G. Pol, Naperville, IL (US); Donald C. Cronauer, Naperville, IL (US); Muruganathan Ramanathan, Knoxville, TN (US)

(73) Assignee: UCHICAGO ARGONNE, LLC, Chicago, IL (US)

( * ) Notice: Subject to any disclaimer, the term of this patent is extended or adjusted under 35 U.S.C. 154(b) by 1180 days.

(21) Appl. No.: 13/247,759

(22) Filed: Sep. 28, 2011

(65) Prior Publication Data

US 2013/0079577 A1    Mar. 28, 2013

(51) Int. Cl.

| | |
|---|---|
| *C07C 1/20* | (2006.01) |
| *B01J 21/06* | (2006.01) |
| *C01G 19/02* | (2006.01) |
| *C01G 23/047* | (2006.01) |
| *B82Y 30/00* | (2011.01) |
| *C07C 1/12* | (2006.01) |

(Continued)

(52) U.S. Cl.
CPC ............... *B01J 21/063* (2013.01); *B01J 23/06* (2013.01); *B01J 23/10* (2013.01); *B01J 23/14* (2013.01); *B01J 23/745* (2013.01); *B01J 35/004* (2013.01); *B01J 35/0013* (2013.01); *B01J 37/08* (2013.01); *B01J 37/084* (2013.01); *B01J 37/14* (2013.01); *B82Y 30/00* (2013.01); *C01F 17/0043* (2013.01); *C01G 19/02* (2013.01); *C01G 23/047* (2013.01); *C07C 1/12* (2013.01); *C01P 2002/54* (2013.01); *C01P 2002/72* (2013.01); *C01P 2002/82* (2013.01); *C01P 2002/85* (2013.01); *C01P 2004/04* (2013.01); *C01P 2004/64* (2013.01); *C01P 2006/80* (2013.01); *C07C 2521/06* (2013.01); *C07C 2523/06* (2013.01); *C07C 2523/10* (2013.01); *C07C 2523/14* (2013.01); *C07C 2523/745* (2013.01); *Y02P 20/52* (2015.11)

(58) Field of Classification Search
None
See application file for complete search history.

(56) References Cited

U.S. PATENT DOCUMENTS

| | | |
|---|---|---|
| 5,266,175 A | 11/1993 | Murphy |
| 5,591,250 A | 1/1997 | Stern et al. |

(Continued)

OTHER PUBLICATIONS

Chai et al, Photocatalytic property of $TiO_2$ loaded with $SnO_2$ nanoparticles, 2006, vol. 17, pp. 323-326.*

(Continued)

*Primary Examiner* — Melvin C Mayes
*Assistant Examiner* — Stefanie Cohen
(74) *Attorney, Agent, or Firm* — Olson & Cepuritis, Ltd.

(57) ABSTRACT

In one preferred embodiment, a photocatalyst for conversion of carbon dioxide and water to a hydrocarbon and oxygen comprises at least one nanoparticulate metal or metal oxide material that is substantially free of a carbon coating, prepared by heating a metal-containing precursor compound in a sealed reactor under a pressure autogenically generated by dissociation of the precursor material in the sealed reactor at a temperature of at least about 600° C. to form a nanoparticulate carbon-coated metal or metal oxide material, and subsequently substantially removing the carbon coating. The precursor material comprises a solid, solvent-free salt comprising a metal ion and at least one thermally decomposable carbon- and oxygen-containing counter-ion, and the metal of the salt is selected from the group consisting of Mn, Ti, Sn, V, Fe, Zn, Zr, Mo, Nb, W, Eu, La, Ce, In, and Si.

3 Claims, 10 Drawing Sheets

(51) Int. Cl.
  *C01F 17/00*   (2006.01)
  *B01J 37/08*   (2006.01)
  *B01J 37/14*   (2006.01)
  *B01J 23/06*   (2006.01)
  *B01J 23/10*   (2006.01)
  *B01J 23/14*   (2006.01)
  *B01J 23/745*  (2006.01)
  *B01J 35/00*   (2006.01)

(56) References Cited

U.S. PATENT DOCUMENTS

| | | | |
|---|---|---|---|
| 5,855,815 | A | 1/1999 | Park et al. |
| 5,938,819 | A | 8/1999 | Seery |
| 2004/0224145 | A1* | 11/2004 | Weir et al. .................. 428/323 |
| 2009/0068080 | A1 | 3/2009 | Faulkner |
| 2010/0178232 | A1 | 7/2010 | Pol et al. |
| 2011/0104553 | A1 | 5/2011 | Pol et al. |
| 2011/0104576 | A1 | 5/2011 | Johnson et al. |

OTHER PUBLICATIONS

Allen et al, Photocatalytic Surfaces: Environmental Benefits of Nanotitania, 2009, The Open Materials Science Journal, 3, 6-27.*

Li et al, preperation and properties of a nano TiO2/Fe3o4 composite superparamagnetic photocatalyst, 2009, rare metals, vol. 28, No. 5, p. 423.*

Channei et al, Synthesis and Characterization of Fe-doped CeO2 Nanoparticles and Their photocatalytic Activities, 2010, Proceedings of the 2010 5th IEEE International Conference on Nano/Micro Engineered and Molecular Systems Jan. 20-23.*

Nirmala et al, Photocatalytic Activity of ZnO Nanopowders Synthesized by DC Thermal Plasma, 2010, African Journal of Basic & Applied Sciences 2 (5-6): 161-166.*

Lee et al, Enhancing the Sensitivity of Oxygen Sensors through the Photocatalytic Effect of SnO2/TiO2 Film, 2005, materials transactions, vol. 46, No. 8, pp. 1942-1949.*

S.S. Tan et al., Photocatalytic Reduction of Carbon Dioxide Into Gaseous Hydrocarbon Using TiO2 Pellets, Catalysis Today 115 (2006), 269-273.

O.K. Varghese et al., High-Rate Solar Photocatalytic Conversion of CO2 and Water Vapor to Hydrocarbon Fuels, Nano Letters, vol. 9, No. 2 (2009) 731-737.

T. Inoue et al., Photoelectrocatalytic Reduction of Carbon Dioxide in Aqueous Suspensions of Semiconductor Powders, Nature, vol. 277 (1979) 637-638.

G. Centi et al., Electrocatalytic Conversion of CO2 to Long Carbon-Chain Hydrocarbons, Green Chem., 9 (2007), 671-678.

* cited by examiner

AUTOGENIC REACTION SYNTHESIS OF PHOTOCATALYSTS FOR SOLAR FUEL GENERATION

CONTRACTUAL ORIGIN OF THE INVENTION

The United States Government has rights in this invention pursuant to Contract No. DE-AC02-06CH11357 between the United States Government and UChicago Argonne, LLC representing Argonne National Laboratory.

FIELD OF THE INVENTION

This invention relates to the energy efficient photocatalytic conversion of carbon dioxide gas and water vapor to methane and other hydrocarbon fuels, particularly promoted by sunlight (referred to herein as "solar-derived fuel" or "solar fuel"). In particular, the invention relates to wide band-gap photocatalytic materials, as well as the synthesis and surface modification thereof, as materials for promoting solar fuel production.

BACKGROUND OF THE INVENTION

As developing countries begin to prosper, fossil fuels will continue to be the primary source of the world's energy. Large deposits of coal throughout the world and the United States are relatively inexpensive and geopolitically stable. The environmental costs of burning coal, however, can be large. Carbon dioxide, which is formed in the conversion of stored chemical energy in fossil fuels to electrical energy, is generally accepted to be a "greenhouse" gas and a major contributor to global warming. Energy efficient capture and/or conversion of carbon dioxide is therefore an important technical challenge. Carbon dioxide is an extremely stable compound at standard conditions, and a large amount of energy is required to reduce it.

Titanium dioxide is a large band-gap semiconductor, which absorbs ultraviolet radiation to form an electron-hole pair. The solar-generated charge carrier can be transferred to adsorbed surface molecules, such as water or carbon dioxide, to promote oxidation and reduction reactions, for example reduction of carbon dioxide to methane or other hydrocarbons (e.g., ethane). To date, the photocatalytic reduction of carbon dioxide is highly inefficient due to limitations in the solar spectrum absorption, electron-hole recombination events, and charge transfer of uncombined electron-hole pairs to adsorbed molecular species on the titanium oxide surface.

In recent years, effort has been made to improve the efficiency of photocatalytic reduction of carbon dioxide (also referred to herein as "solar fuel conversion"). Cocatalyst structures consisting of a combination of metal oxide semiconductors and noble metals, and highly doped metal oxide semiconductors have been proposed in order to "tune" the adsorption edge (i.e., bulk band gap) of the photocatalysts. These approaches reportedly have increased the conversion efficiency to some degree; however, inefficient conversion has remained a significant impediment to widespread commercialization of this technology.

Consequently, there is an ongoing need for improved catalysts for photochemical (particularly solar) reduction of carbon dioxide to hydrocarbon fuels such as methane. The present invention addresses this ongoing need.

SUMMARY OF THE INVENTION

The present invention provides wide band-gap photocatalytic materials useful for catalyzing the solar conversion of carbon dioxide and water to hydrocarbons (particularly methane) and oxygen. The materials of the invention are prepared by reaction of one or more dry, solvent-free chemical precursor powders in a sealed reactor at elevated temperature and autogenically generated high pressure resulting dissociation of the precursor materials in the closed reactor at elevated temperature in a sealed reactor at high temperatures and high pressures generated autogenically by vaporization of precursor materials in the reactor.

A wide range morphologies, particle shapes and sizes, and unique 'core-shell' materials, can be synthesized and are of varying importance for the efficient transfer of solar energy to fuels. The sun is a significant source of energy, which is free, abundant, and renewable. The amount of energy consumed by the Earth's population in one year is supplied by the sun in just one minute. New technologies, such as solar energy-promoted fuel production, will be critical component of a comprehensive energy plan for world. The photocatalytic materials produced by the autogenic reactor have been shown to have high conversion efficiencies and may be utilized in flue gas or transportation exhaust to maintain carbon neutrality in the burning of fossil fuels.

In one preferred embodiment, the photocatalyst comprises at least one nanoparticulate metal or metal oxide material that is substantially free of a carbon coating, and which is prepared by heating a metal-containing precursor compound in a sealed reactor under a pressure autogenically generated by dissociation of the precursor material in the sealed reactor at a temperature of at least about 400° C. to form a nanoparticulate carbon-coated metal or metal oxide material and subsequently substantially removing the carbon coating from the material. The precursor material comprises a solid, solvent-free salt comprising a metal ion and at least one thermally decomposable carbon- and oxygen-containing counter-ion. The metal is selected from the group consisting of Mn, Ti, Sn, V, Fe, Zn, Zr, Mo, Nb, W, Eu, La, Ce, In, and Si. Preferably, the metal oxide is selected from the group consisting of $Mn_3O_4$, $TiO_2$, $SnO_2$, $V_2O_3$, $V_2O_5$, $Fe_3O_4$, $Fe_2O_3$, ZnO, $ZrO_2$, $MoO_2$, $MoO_3$, $Nb_2O_3$, $Eu_2O_3$, $La_2O_3$, $CeO_2$, $La_2O_3$, $SiO_2$, and a tungsten oxide (e.g., anatase $TiO_2$, rutile $SnO_2$, or a combination thereof). The tungsten oxide prepared under autogenic pressure conditions has a mixed valence, with an empirical formula close to $WO_3$ (e.g., approximately $W_{24}O_{68}$) and may also be referred to herein for convenience as $WO_x$ (with x being approximately equal to 3). Optionally, the metal oxide material can include one or more promoters selected from noble metals and transition metals.

In some embodiments, the counter ion is an organic material (e.g., carboxylate ion such as acetate or oxyacetoacetonate, an alkoxide such as methoxide or ethoxide, and the like) or an inorganic material (e.g. carbonate ion or bicarbonate ion), or a combination of two or more such ions.

In other embodiments the precursor material is selected from a titanium salt, a tin salt, a cerium salt, a zinc salt, an iron salt, and a combination of two or more of the foregoing salts.

In one preferred embodiment the metal oxide comprises anatase $TiO_2$ substantially free of a carbon coating, formed by thermal reaction of titanium oxyacetoacetonate in a sealed reactor at a temperature of about 700° C. under an autogenically generated pressure of up to about 150 pounds-per-square-inch (psi) to form a nanoparticulate carbon-coated anatase $TiO_2$ powder, and subsequently substantially removing the carbon coating (e.g., removing at least 90%. 95%, 97%, 98%, 99% or more of the carbon), e.g., by heating the carbon-coated powder in air at a temperature of about 450° C. for a period of time sufficient to remove substantially all of the carbon coating from the anatase $TiO_2$. Preferably, the anatase TiO$_2$ powder comprises particles having a particle size in the range of about 10 to about 30 (e.g., about 25 nm).

In another preferred embodiment the metal oxide comprises rutile SnO$_2$ substantially free of a carbon coating, formed by thermal reaction of tin ethoxide in a sealed reactor at a temperature of about 600° C. under an autogenically generated pressure of up to about 100 psi to form a nanoparticulate carbon-coated rutile SnO$_2$ powder, and subsequently substantially removing the carbon coating (e.g., removing at least 90%. 95%, 97%, 98%, 99% or more of the carbon), e.g., by heating the carbon-coated powder in air at a temperature of about 450° C. for a period of time sufficient to remove substantially all of the carbon coating from the rutile SnO$_2$. Preferably, the rutile SnO$_2$ powder comprises particles having a particle size in the range of about 10 to about 20 nm.

In yet another preferred embodiment, the metal oxide comprises a mixture of anatase TiO$_2$ and rutile SnO$_2$ (e.g., about 95:5 to about 50:50 wt/wt TiO$_2$:SnO$_2$, for example about 95 percent by weight (wt %) of the TiO$_2$ and about 5 wt % of the SnO$_2$); or the metal oxide comprises CeO$_2$, ZnO or Fe$_3$O$_4$.

In another aspect, the present invention provides a method of converting carbon dioxide into a hydrocarbons such as methane, ethane and the like comprising exposing a gaseous mixture of carbon dioxide and water to sun light in the presence of a photocatalyst of at a temperature sufficient to catalyze reduction of carbon dioxide to methane, wherein the photocatalyst comprises at least one nanoparticulate metal or metal oxide material that is substantially free of a carbon coating, prepared by heating a metal-containing precursor compound in a sealed reactor under a pressure autogenically generated by dissociation of the precursor material in the sealed reactor at a temperature of at least about 400° C. to form a nanoparticulate carbon-coated metal or metal oxide material, and subsequently substantially removing the carbon coating from the material as described herein. The precursor material comprises a solid, solvent-free salt comprising a metal ion and at least one thermally decomposable carbon- and oxygen-containing counter-ion, and the metal of the salt is selected from the group consisting of Mn, Ti, Sn, V, Fe, Zn, Zr, Mo, Nb, W, Eu, La, Ce, In, and Si.

In some preferred method embodiments, the metal oxide is selected from the group consisting of Mn$_3$O$_4$, TiO$_2$, SnO$_2$, V$_2$O$_3$, V$_2$O$_5$, Fe$_3$O$_4$, Fe$_2$O$_3$, ZnO, ZrO$_2$, MoO$_2$, MoO$_3$, Nb$_2$O$_3$, Eu$_2$O$_3$, La$_2$O$_3$, CeO$_2$, In$_2$O$_3$, SiO$_2$, and WO$_x$. Optionally the oxide material can include one or more promoters such as noble metals and transition metals.

In other preferred method embodiments, the metal oxide comprises anatase TiO$_2$ substantially free of a carbon coating, formed by thermal reaction of titanium oxyacetoacetonate in a sealed reactor at a temperature of about 700° C. under an autogenically generated pressure of up to about 150 pounds-per square-inch (psi) to form a nanoparticulate carbon-coated anatase TiO$_2$ powder, and subsequently substantially removing the carbon coating.

In yet other preferred method embodiments, the metal oxide comprises rutile SnO$_2$ substantially free of a carbon coating, formed by thermal reaction of tin ethoxide in a sealed reactor at a temperature of about 600° C. under an autogenically generated pressure of up to about 100 pounds-per square-inch (psi) to form a nanoparticulate carbon-coated rutile SnO$_2$ powder, and subsequently substantially removing the carbon coating.

A mixed metal oxide comprising anatase TiO$_2$ and rutile SnO$_2$, as well as CeO$_2$, ZnO, and Fe$_3$O$_4$ prepared as described herein also can be utilized as the catalyst in the methods of the present invention.

DETAILED DESCRIPTION OF THE PREFERRED EMBODIMENTS

This invention relates to wide band-gap photocatalytic materials, their synthesis and their surface modifications, as well as to use of these materials to catalyze the efficient conversion of carbon dioxide and water to hydrocarbon fuels by solar energy (i.e., production of "solar fuels"). The photocatalysts of the present invention have particular application in transportation and station power production, to effectively recycle and reduce or eliminate the output of carbon dioxide to the atmosphere.

The photocatalytic reduction of carbon dioxide to methane (and other hydrocarbon chains) is not fully understood and is a complex multistep reaction involving multiple reaction pathways and mechanisms. It is generally accepted, however, that upon the absorption of a photon an electron-hole pair is formed which serves as reductant and oxidant, respectively, for the overall reaction: $CO_2+2H_2O+8h^++8e^-=2O_2+CH_4$. The initial mechanistic step is believed to be the formation of protons (H$^+$) [T. Inoue, et al, Nature 277, 637 (1979)] and an activated carbon dioxide ion (CO$_2^-$) [G. Centi, et al., Green Chem. 9(6), 671 (2007)].

The photocatalytic materials of the present invention exhibit conversion efficiencies for the solar-promoted conversion of humidified carbon dioxide to methane (and ethane) far in excess to those generally reported in the open literature. The photocatalysts of the invention are prepared by solvent-free, thermal conversion of precursor materials under autogenically-produced pressure. The photocatalysts include a variety of useful particulate oxides including Mn$_3$O$_4$, TiO$_2$, SnO$_2$, V$_2$O$_3$, V$_2$O$_5$, Fe$_3$O$_4$, Fe$_2$O$_3$, ZnO, ZrO$_2$, MoO$_2$, MoO$_3$, Nb$_2$O$_3$, Eu$_2$O$_3$, La$_2$O$_3$, CeO$_2$, In$_2$O$_3$, SiO$_2$, and WO$_x$, and the like, in distinct particle sizes, particle shapes, and structures. Particulate metal sulfides, and particulate metals such as Ni, Co, Sn, Pt, Ru, Pd, Zr, Mg, Si either substantially pure or coated by carbon also can be prepared using the autogenic reactions as described herein. The photocatalysts of the present invention include particulate metal oxide materials, combinations of a particulate metal oxide with a metal, combinations of metals, and metal doped oxides, which are prepared under the autogenic reaction conditions described herein.

In a first embodiment, the invention relates to wide band gap semiconductor photocatalysts produced by the autogenic pressure reaction techniques described herein, particularly TiO$_2$ nanoparticles. Further embodiments include, but are not limited to, nano-engineered surface-activated oxide powders, which minimize interaction energy with molecular CO$_2$ and promote intermediate species formation. An example of this approach is transition metal surface-doping of TiO$_2$. In other embodiments, the photocatalyst comprises particulate sulfides of metals such as Cd, Zn, and Sn synthesized by the autogenic processes described herein. An autogenically prepared TiO$_2$-based catalyst exhibited a surprisingly high photocatalytic efficiency in the conversion of carbon dioxide and water to solar fuel, such as methane and ethane.

The following examples are provided to illustrate certain aspects of the present invention, but are not to be construed as limiting the claims appended hereto.

Example 1

TiO$_2$ (Anatase) Before and After Removal of Carbon Coating

Carbon-encapsulated anatase TiO$_2$ nanoparticles were prepared by thermolysis of a single precursor, titanium (IV) oxyacetyl acetonate (TiO[C$_5$H$_8$O$_2$]$_2$), in a sealed reactor (Haynes 230 alloy, 10 mL capacity) fitted with a pressure gauge. Two grams of the precursor material were placed in the reactor under a nitrogen atmosphere. After being tightly sealed, the reactor was placed in a furnace and heated to 700° C. at a heating rate of 30° C./minute. The temperature of the reactor was held at 700° C. for 1 hour, during which a maximum autogenic pressure of 150 psi (10.2 atm) was reached. Thereafter, the reactor was cooled gradually to room temperature, and the remaining pressure was released before it was opened to collect the product (a black powder). A thermogravimetric analysis (TGA, Seiko Exstar 6000) of the resulting black powder revealed that the as-prepared TiO$_2$ product contained approximately 30% carbon by weight (i.e., primarily as a coating of the TiO$_2$ particles). A portion of the product subsequently was heated further in air at 450° C. for 1 hour to reduce the amount of carbon (by oxidation of the carbon to CO$_2$), leaving only a thin layer on the TiO$_2$ nanoparticles. A TGA of the oxidized product showed that approximately 5 wt. % carbon remained in the sample.

Figure 1:
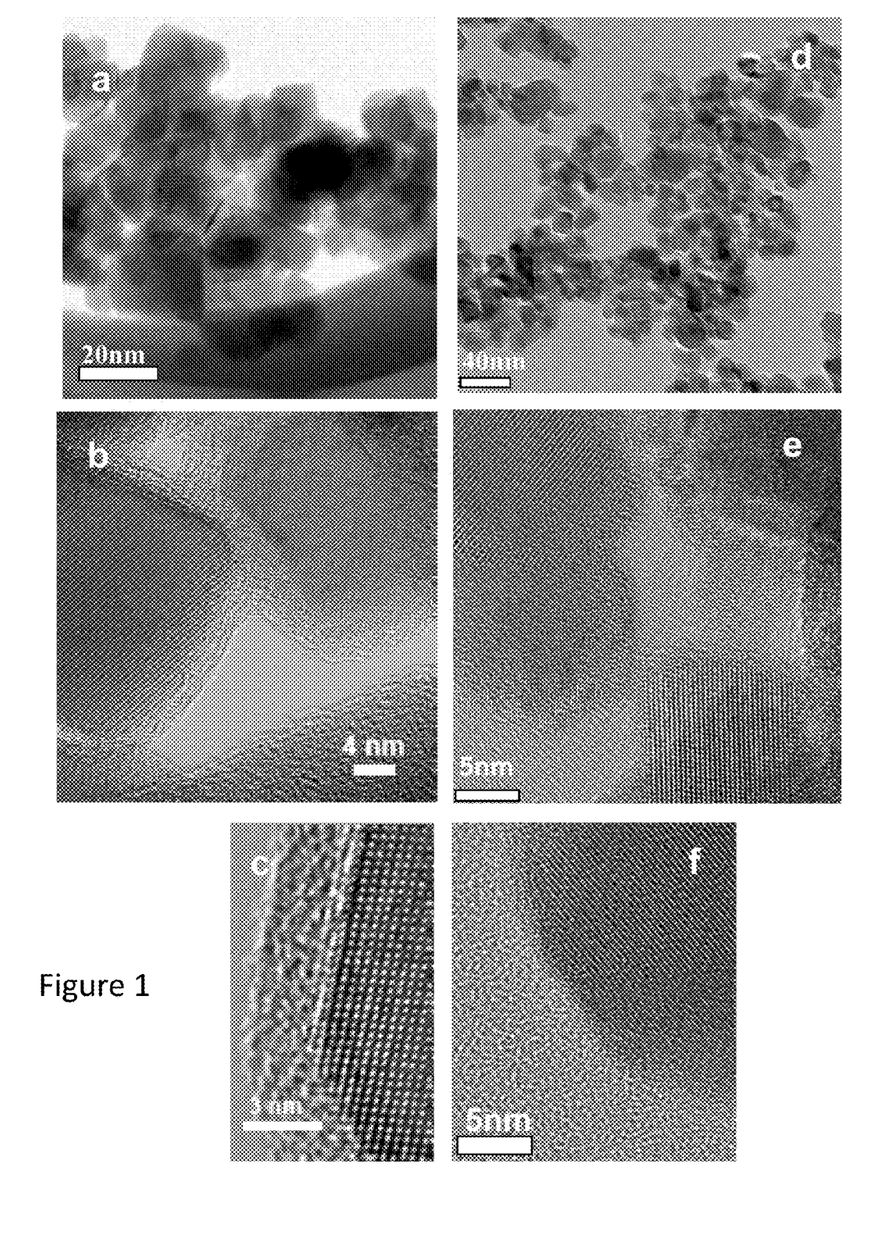
FIG. 1: Transmission electron micrographs of solar catalysts (TiO$_2$ nanoparticles) prepared by the autogenic reaction. The TiO$_2$—C (Panels a-c) are produced from the one step dissociation of titanium (IV) oxyacetyl acetonate (TiO[C$_5$H$_8$O$_2$]$_2$). The TiO$_2$ nanoparticles (Panels d-f) are achieved after oxidation of carbon at 500° C.

A high-resolution transmission electron micrographic (TEM) image (FIG. 1a) shows that most of the individual TiO$_2$—C particles are, on average, less than about 20 nm in dimension, and that they are highly crystalline, which is consistent with the XRD data as described below. FIGS. 1b and c are, in general, representative images of the whole TiO$_2$—C sample, and demonstrate that most, if not all, of the TiO$_2$ nanoparticles are encapsulated by a layer of amorphous carbon. In this case, the coating typically is about 2-4 nm in thickness. The thickness of the coating can be tailored by the temperature and heating period used to oxidize the initially formed carbon coating.

As described below, a very small photocatalytic effect on CO$_2$ photoreduction was observed using the carbon-coated TiO$_2$. Therefore, the carbon coating was substantially completely removed by further oxidation in air at 450° C. for an additional 2 hours. The TEM image (FIG. 1d) of the carbon-free TiO$_2$ shows that most of the primary TiO$_2$ particles are around 25 nm in diameter. High-resolution TEM images (FIGS. 1e and f) show that the carbon was substantially completely removed from the surface of TiO$_2$ particles, leaving behind highly crystalline particles. The obtained powder remained gray in color and not the bright white appearance of commercial TiO$_2$. It is believed that a very small amount of carbon is doped into the crystal structure of the TiO$_2$, resulting in the gray color. Consequently, the TiO$_2$ materials formed under the autogenic conditions described herein constitutes a composition of matter that is distinct from TiO$_2$ made by the standard methods of the prior art.

Example 2

Composition and Structure of Anatase TiO$_2$ Photocatalyst

Figure 2:
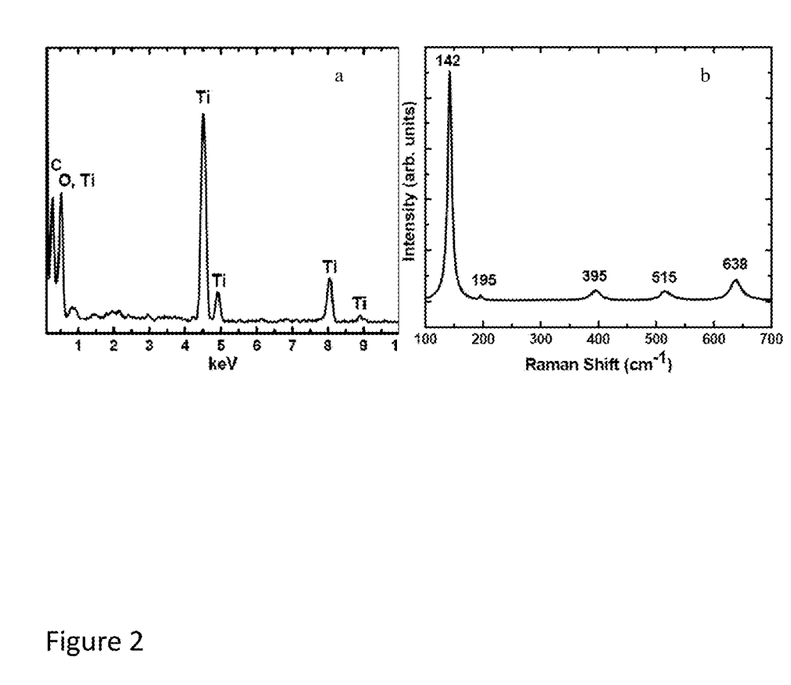
FIG. 2: Energy dispersive X-ray analysis (EDS) confirmed that the TiO$_2$ nanoparticles are composed of only Ti and O elements without other impurities (the carbon signal is obtained from the sample supported TEM grid).

An elemental analysis of the substantially carbon-free TiO$_2$ nanoparticle material of Example 1, obtained by energy dispersive x-ray spectroscopy (EDS), showed only C, O, and Ti, confirming the purity of the TiO$_2$ produced as described herein. The small presence of carbon (inset in FIG. 2a) is primarily due to the supported sample grid. A Raman spectrum of the TiO$_2$ same product, exhibited the strongest band at 142 cm−1 and additional bands at 195, 395, 515, and 638 cm−1, which is characteristic of pure anatase TiO$_2$. It has been reported that the phase transformation of pure anatase to rutile occurs at around 600° C. Thus, the Raman data demonstrate that the TiO$_2$ particles formed under the autogenic reaction conditions described herein surprisingly remained in the anatase phase even though the reaction temperature (about 700° C.) was about 100 degrees higher than the reported phase transition temperature for conversion of anatase to rutile. The suppression of the phase transition likely is due to the presence of a carbon shell around the TiO$_2$ nanoparticles during the formation reaction. Similarly, the combustion of the carbon coating at 450° C. in air did not induce a phase change from anatase to rutile.

Example 3

SnO$_2$ Nanoparticles: Before and After Removal of Carbon Coating

Carbon-coated SnO$_2$ nanoparticles were prepared by thermolysis of a single precursor, tin ethoxide, Sn(OC$_2$H$_5$)$_2$, in a the same autogenic reactor setup used in Example 1. After being tightly sealed, the pressure gauge of the reactor was attached and the reactor was placed in a furnace to heat up to about 600° C. with a heating rate of about 20° C./minute. The temperature of the reactor was held at 600° C. for 1 hour, during which time a maximum autogenic pressure of about 100 psi was reached. Thereafter, the reactor was cooled gradually to room temperature (over about 4 hours), and the remaining pressure was released before the reactor was opened to afford carbon-coated $SnO_2$ nanoparticles ($SnO_2$—C) as a black powder. A sample of the carbon-coated material was heated in air at about 450° C. to remove the carbon coating as in Example 1.

Figure 3:
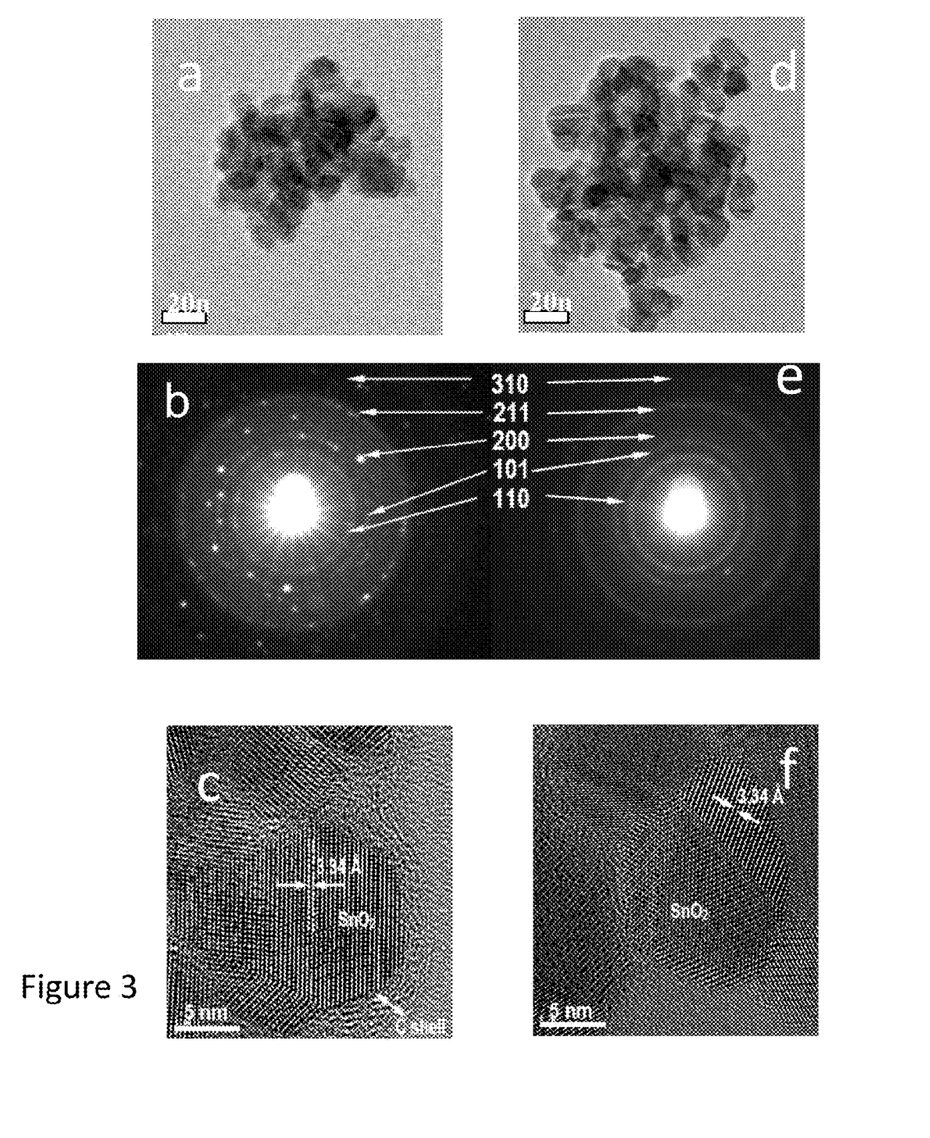
FIG. 3: Transmission electron micrographs of solar catalysts (SnO$_2$ nanoparticles) prepared by the autogenic reaction. The SnO$_2$—C (Panels a-c) are produced from the one step dissociation of tin ethoxide, Sn(OC$_2$H$_5$)$_2$. The SnO$_2$ nanoparticles (Panels d-f) are achieved after oxidation of carbon at 500° C.

The particle diameters and structure of the $SnO_2$—C and $SnO_2$ particles were studied by employing the HR-TEM technique (FIG. 3). Lower magnification micrographs show nanocrystallites of about 10-20 nm size (FIG. 3a,d). Electron diffraction patterns showed clear diffraction rings, indexed according to the crystalline structure of tetragonal $SnO_2$ (FIG. 3b,e). The higher magnification images of $SnO_2$—C sample (FIG. 3c) show the presence of a thin shell (about 1-4 nm thickness), of a less dense material having a disordered lattice surrounding the well-ordered tin oxide nanocrystallite lattice. The lattice images of tin oxide nanocrystallites show the identical lattice spacing's before and after thermal treatment to remove carbon (FIGS. 3c,f). The $SnO_2$ nanoparticles were also tested for the photocatalytic conversion of $CO_2$ to methane as described below.

Example 4

Structure of $SnO_2$ Photocatalyst

Figure 4:
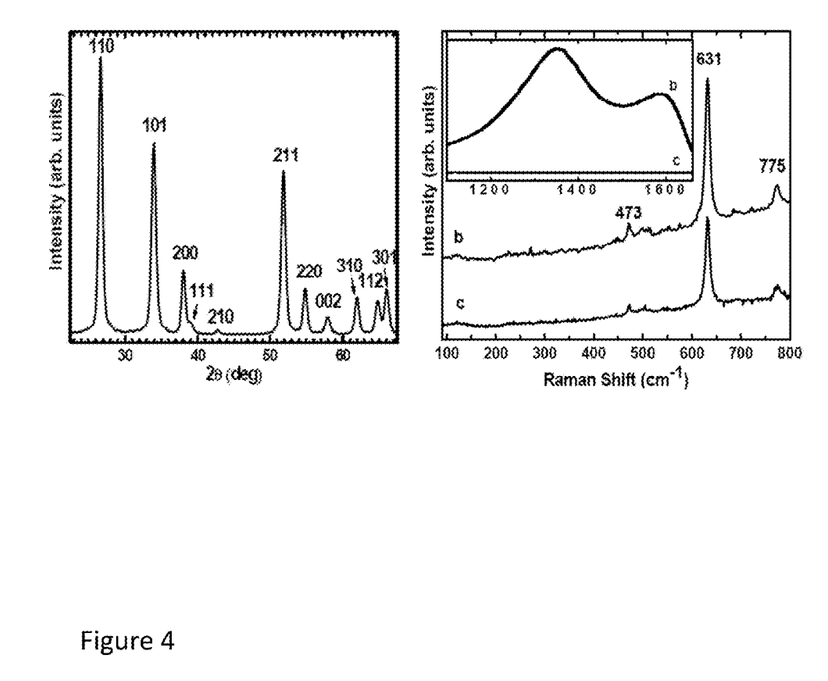
FIG. 4: (a) The powder XRD pattern of SnO$_2$—C sample, (b) Raman spectrum of SnO$_2$—C and (c) SnO$_2$ samples (inset shows the bands in a carbon frequency range).

Since the obtained XRD patterns for the $SnO_2$—C and $SnO_2$ nanoparticles are analogous; a representative XRD pattern of $SnO_2$—C sample is presented in FIG. 4a. All the diffraction peaks for $SnO_2$—C sample are indexed to the tetragonal rutile structure of $SnO_2$ with the space group P42/mnm (136). The broad peaks indicate that the as-prepared powder is composed of small size $SnO_2$ crystallites. No characteristic peaks peculiar to elemental Sn or other tin oxide impurities were observed, confirming the purity of the as-prepared $SnO_2$—C product. The graphite peak at 26 two theta is overlapped with the 110 reflections of $SnO_2$.

Raman spectroscopy was employed to study the nature of carbon (insert of FIG. 4b) in the $SnO_2$—C material. The Raman spectrum exhibited a graphitic band (G-band) at 1594 $cm^{-1}$ and disordered (D-band) carbon band at 1343 $cm^{-1}$ (insert of FIG. 4b-c). The peak at 1343 $cm^{-1}$ is associated with the vibration of carbon atoms with dangling bonds for the in-plane terminated disordered graphite. The 1594 $cm^{-1}$ band corresponding to the $E_{2g}$ mode, is closely related to the vibration of all the $sp^2$-bonded carbon atoms in a 2D hexagonal lattice, as in a graphene layer. The broad and strong D-band confirms the highly disordered nature of the carbon coating, which likely is due to the low (600° C.) synthetic temperature utilized to prepare the material. The Raman spectra of the $SnO_2$—C and $SnO_2$ nanostructures are shown in FIG. 4b-c, and have three fundamental Raman scattering peaks at 473, 631, and 775 cm-1, corresponding respectively to the $E_g$, $A_{1g}$, and $B_{2g}$ modes of rutile $SnO_2$ structure. The disappearance of both carbon bands clearly indicates the complete combustion/removal of carbon in the sample that was air-oxidized (FIG. 4c).

Example 5

Optical Properties of $SnO_2$ Photocatalysts

Figure 5:
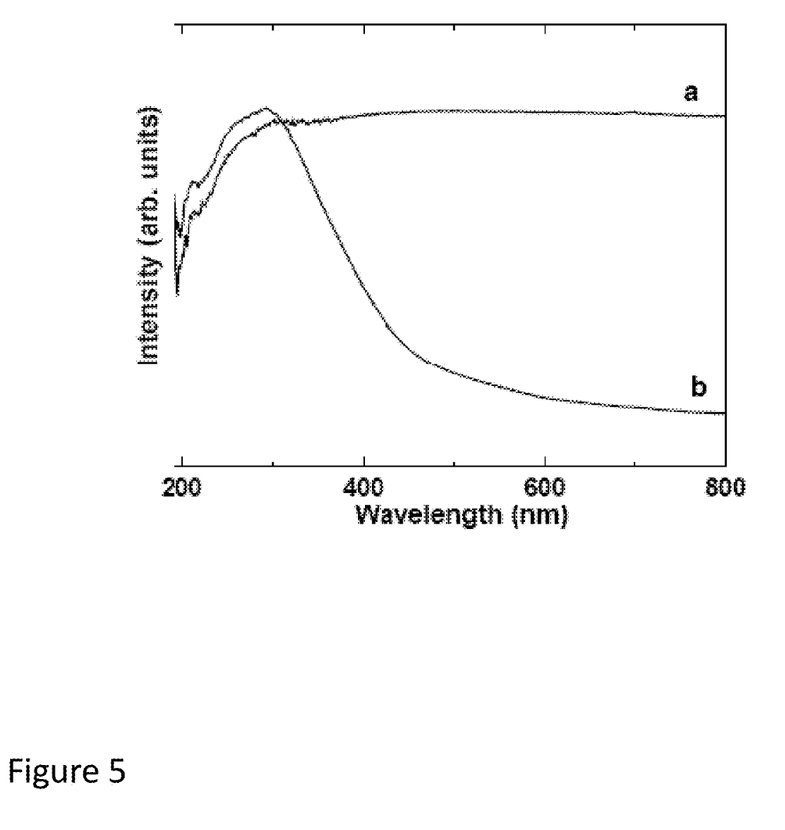
FIG. 5: The optical absorbance spectra of (a) SnO$_2$—C sample and (b) SnO$_2$ sample.

Due to excellent optical, electrical, and chemical stability properties, semiconducting (Eg=3.62 eV at 300 K) tin oxide ($SnO_2$) nanostructures have been widely used for chemical sensors, batteries, catalysts, transistors and for photoluminescence. FIGS. 5a and 5b illustrate the optical absorption of the rutile $SnO_2$—C and $SnO_2$ nanoparticles, respectively. $SnO_2$ sample reveals an absorption edge around 300 nm as expected for $SnO_2$ nanoparticles. It is worth mentioning that the $SnO_2$—C sample absorbs in the whole visible region due to the presence of surface carbon. The absorption for $SnO_2$ peak is also shifted to higher wavelength for carbon-coated $SnO_2$, as compared with the carbon-free $SnO_2$. The red shift of the absorption edge for the $SnO_2$—C nanocrystals compared to carbon-free $SnO_2$ indicates that this is an inherent property of the $SnO_2$ nanocrystals due to the surface coating of carbon. Both the materials clearly show the UV absorption band of rutile $SnO_2$.

Example 6

Carbon Dioxide Reduction Rates with $TiO_2$ Photocatalyst

Figure 6:
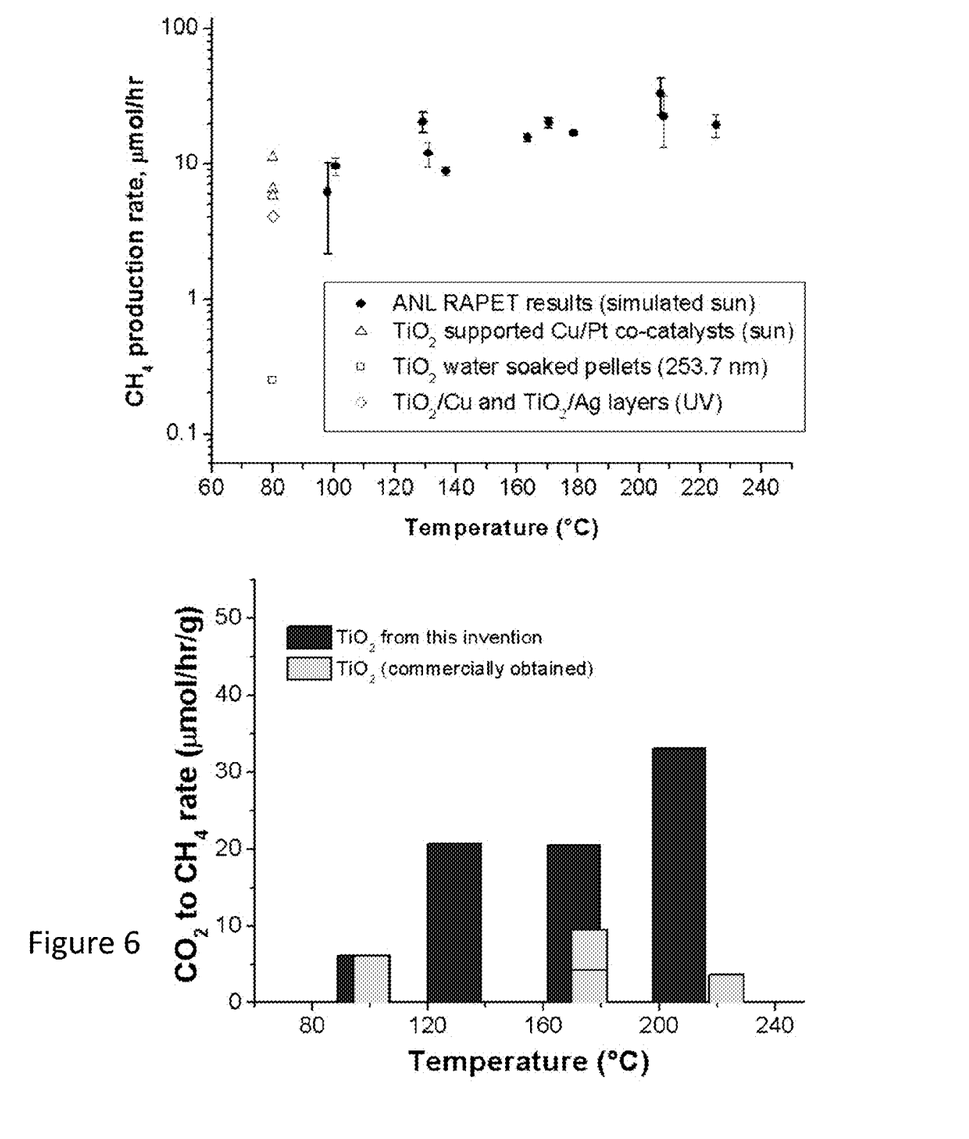
FIG. 6: Conversion efficiencies for typical autogenic reaction derived pure nano-TiO$_2$ photocatalyst as compared to similar materials derived by other techniques and materials engineering enhancements (◇ [S. S. Tan, et al, *Catalysis Today* 115, 269 (2006)], and Δ [O. K. Varghese, et al, *Nano Lett.* 9, 731 (2009)]).

The photocatalytic activity of the carbon-free $TiO_2$ (anatase) of Example 1 for photo-reduction of carbon dioxide to methane was evaluated as described below in Example 10. The carbon-free $TiO_2$ exhibited high $CO_2$ to $CH_4$ conversion rates relative to previously reported co-catalyst and doped catalyst systems, as illustrated in FIG. 6a. Conversion rates of ≥10 μmol/hour were routinely obtained at room temperature and above. Comparison values are indicated in FIG. 6 for conventional prior art $TiO_2$ cocatalysts (composite systems with Pt or Cu). The $TiO_2$ photocatalyst material of Example 1 (i.e., single phase, non-coated) clearly exhibited at a high performance level.

Rates for conversion of $CO_2$ to $CH_4$ obtained in identical testing procedures were compared between $TiO_2$ obtained commercially and the $TiO_2$ as prepared in Example 1 (FIG. 6b). A surprising increase in conversion rate was apparent for $TiO_2$ of this invention relative to the commercial material. This trend was enhanced at elevated temperatures (>200° C.), in which an order of magnitude improvement in conversion efficiency was observed.

Example 7

Carbon Dioxide Reduction Rates with $SnO_2$ Photocatalyst

Figure 7:
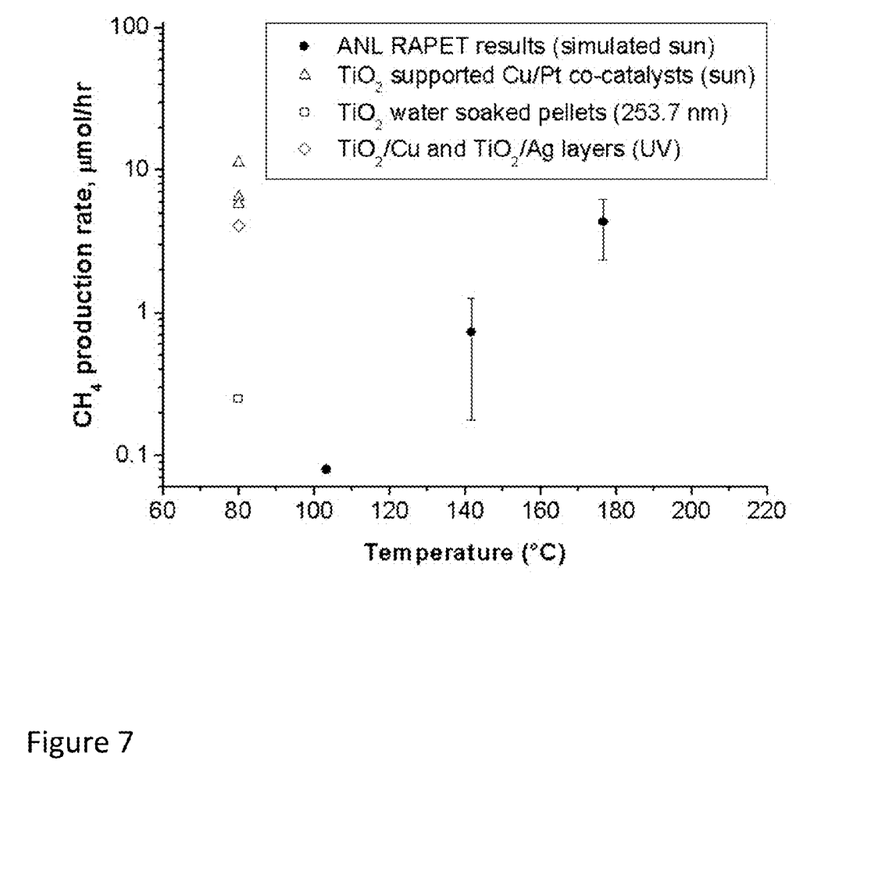
FIG. 7: Conversion efficiencies for typical autogenic reaction derived pure nano-SnO$_2$ photocatalyst as compared to similar materials derived by other techniques and materials engineering enhancements (◇ [S. S. Tan, et al, *Catalysis Today* 115, 269 (2006)], and Δ [0. K. Varghese, et al, *Nano Lett.* 9, 731 (2009)]).

To our knowledge, $SnO_2$ has not been previously reported to be a photocatalyst for the reduction of $CO_2$ to $CH_4$ or other hydrocarbons. The photocatalytic activity of the carbon-free $SnO_2$ of Example 3 was evaluated as described below in Example 10. As shown in FIG. 7, at elevated temperatures, the $SnO_2$ material of Example 3 exhibited comparable conversion rates to $TiO_2$-metal cocatalysts. The conversion rates for the $SnO_2$ material of Example 3 show a large temperature dependence (unlike the $TiO_2$ discussed in Example 6). At room temperature, limited $CO_2$ to $CH_4$ was observed; however, at >180° C. a conversion rate of about 10 μm/hr are obtained.

Example 8

Carbon Dioxide Reduction Rates with a $SnO_2$/$TiO_2$ Photocatalyst

Figure 8:
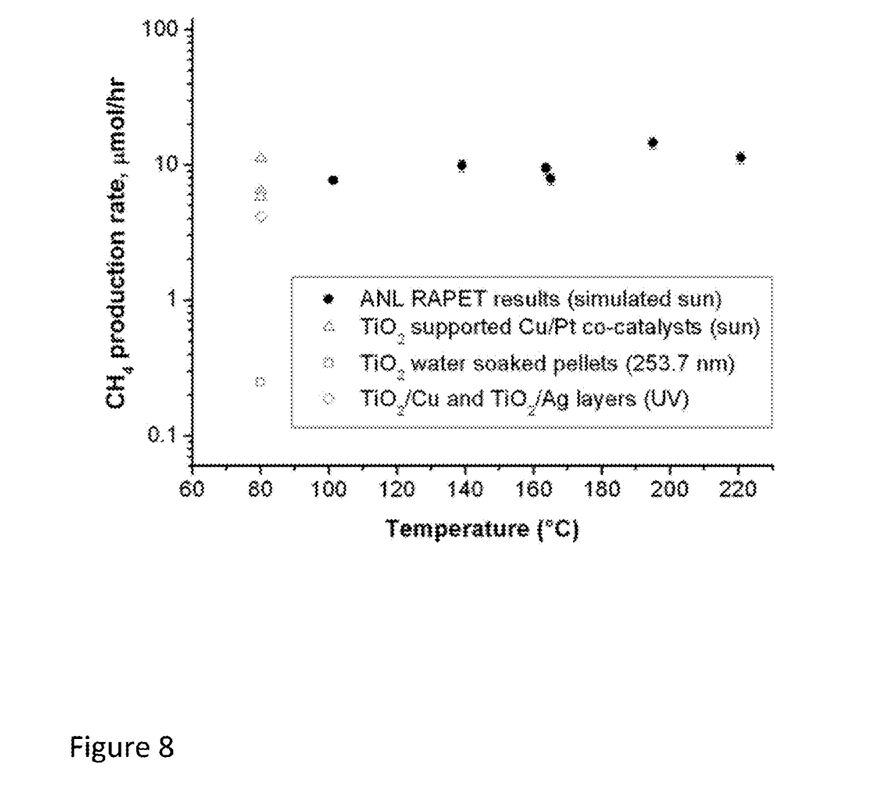
FIG. 8: Conversion efficiencies for typical autogenic reaction derived TiO$_2$—SnO$_2$ nanocomposite photocatalyst as compared to similar materials derived by other techniques and materials engineering enhancements (◇ [S. S. Tan, et al, *Catalysis Today* 115, 269 (2006)], and Δ [O. K. Varghese, et al, *Nano Lett.* 9, 731 (2009)]).

As shown in FIG. 8, a composite of about 95 wt % $TiO_2$ and 5 wt % $SnO_2$ (carbon-free materials from Examples 1 and 3, respectively) exhibited high conversion rates for $CO_2$ reduction similar to those described in Example 6 (i.e., about 10 µmol/hour). There was no evident temperature dependence, and the at low temperatures (<120° C.) the conversion rate was not limited by the $SnO_2$.

Example 9

Carbon Dioxide Reduction Rates with Various Metal Oxides

Figure 9:
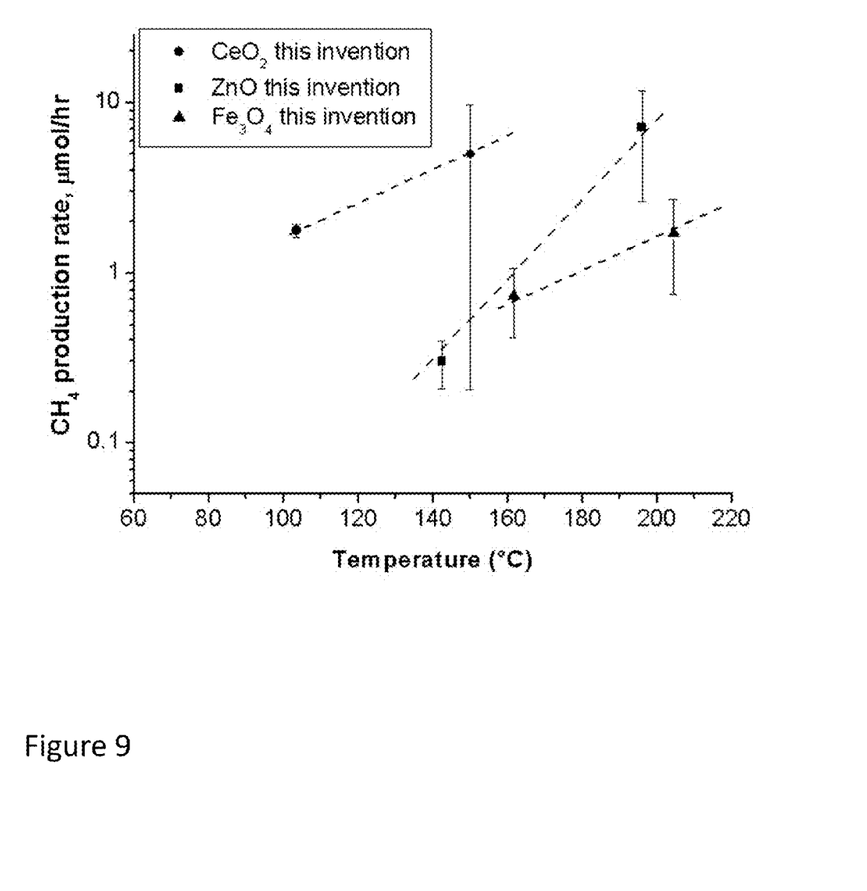
FIG. 9: Conversion efficiencies for ZnO, CeO2 and Fe2O3 photocatalysts of the invention.

A number of different metal oxide materials were prepared under the autogenic pressure method described Examples 1 and 3. FIG. 9 indicates detectable conversion rates for $CO_2$ to $CH_4$ with the different metal oxides, some of which were otherwise unknown to exhibit photocatalytic properties. The exemplary systems evaluated were ZnO, $CeO_2$, and $Fe_3O_4$, the latter of which has been described as a good photocatalyst with limited corresponding reduction rates due to rapid electron-hole recombination. Significant photocatalytic reduction activities were observed by these metal oxide systems, which were prepared from zinc (II) acetate, cerium acetate, and iron (II) oxalate, respectively, at approximately 700° C. under autogenic pressure as described herein for the other materials.

Example 10

Reaction Chamber for $CO_2$ to $CH_4$ Conversion Via Photocatalyst

Figure 10:
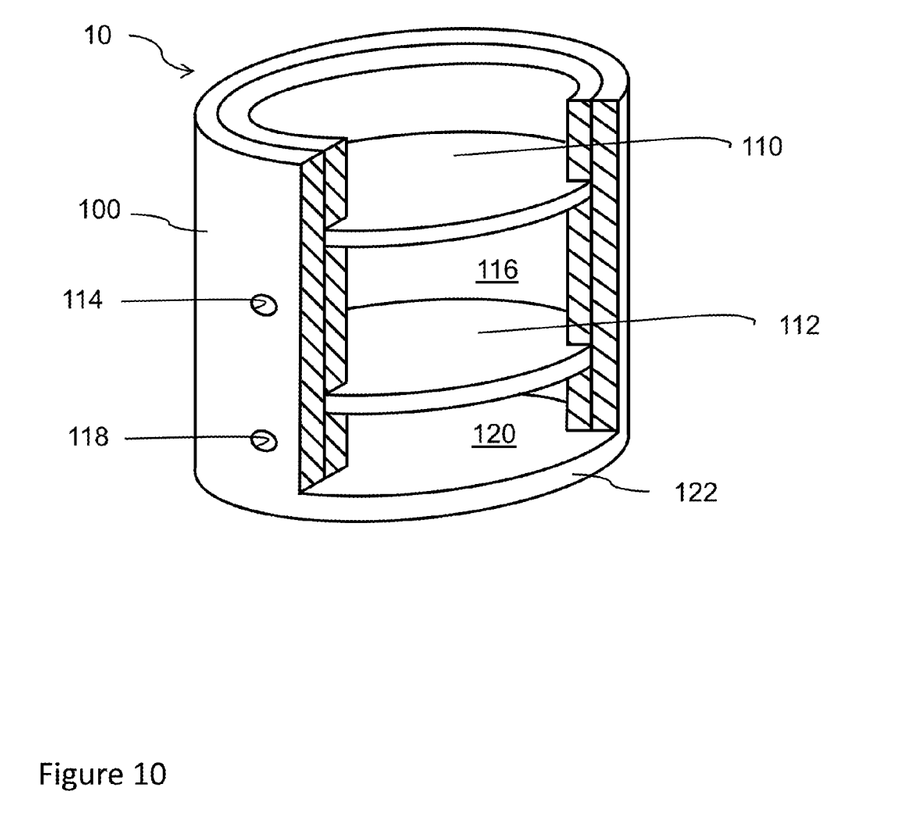
FIG. 10: Schematic diagram of photoreduction reaction chamber.

Photocatalytic performance was evaluated by measuring the rate conversion of a humidified $CO_2$ gas stream to methane utilizing the particulate materials described herein. A schematic illustration of the photocatalytic reduction reactor is shown in FIG. 10. Reactor 10 comprises stainless steel vessel 100 sealed at one end by quartz window 110 and at the other end by plate 122. Fritted glass support 112 is positioned intermediate between window 110 and plate 122, and is adapted to support the powdered catalyst bed (not shown). Gas inlet 114 is in communication with the chamber 116 between quartz window 110 and fitted glass support 112. Gas outlet 118 is in communication with chamber 120 on the other side of fitted glass support 112 from chamber 116. In the laboratory evaluations, simulated solar-spectrum light illuminated a catalyst bed comprising the photocatalysts of the invention through quartz window 110. Humidified carbon dioxide is injected into region 116 through inlet 114. The humidified $CO_2$ flows through the catalyst bed and in converted to hydrocarbons such as methane, which enters chamber 120 and exits the reactor through outlet 118. The carbon dioxide was humidified by passing a stream of the gas through water prior to introducing the carbon dioxide into chamber 116. In a prototype reactor, typical catalyst amounts ranged from 0.7 to 1.5 g of material resulting in a catalyst bed approximately 1 mm thick or less. The frit base and quartz windows in the prototype reactor were 2.5 inches in diameter and the light source approximated the spectrum and intensity of the solar spectrum from the sun at an elevation of 41.81° above the horizon as defined by the American Society for Testing and Materials (ASTM) G173-03 standard. Gas flow rates were in the range of about 10 to 60 mL/min (standard pressure and temperatures) with equivalent system pressures were in the range of about between 2 to 7 psi.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All numerical values obtained by measurement (e.g., weight, concentration, physical dimensions, removal rates, flow rates, and the like) are not to be construed as absolutely precise numbers, and should be considered to encompass values within the known limits of the measurement techniques commonly used in the art, regardless of whether or not the term "about" is explicitly stated. All methods described herein can be performed in any suitable order unless otherwise indicated herein or otherwise clearly contradicted by context. The use of any and all examples, or exemplary language (e.g., "such as") provided herein, is intended merely to better illuminate certain aspects of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A photocatalyst for conversion of carbon dioxide and water into a hydrocarbon and oxygen, the photocatalyst comprising at least one metal oxide material that is substantially free of a carbon coating, prepared by heating a metal-containing precursor compound in a sealed reactor under a pressure autogenically generated by dissociation of the precursor material in the sealed reactor at a temperature of at least about 400° C. to form a nanoparticulate carbon-coated metal or metal oxide material, and subsequently substantially removing the carbon coating; wherein:

the precursor material comprises a solid, solvent-free salt comprising a metal on and at least one thermally decomposable carbon- and oxygen-containing counter-ion;

the metal oxide consists of a mixture of $SnO_2$ nanoparticles and $TiO_2$ nanoparticles; the $SnO_2$ consists essentially of rutile $SnO_2$ that is substantially free of a carbon coating, and is formed by thermal reaction of tin ethoxide in a sealed reactor at a temperature of about 600° C. under an autogenically generated pressure of up to about 100 pounds-per square-inch (psi) to form a nanoparticulate carbon-coated rutile $SnO_2$ powder, and subsequently substantially removing the carbon coating;

the $TiO_2$ consists essentially of carbon-doped anatase $TiO_2$ that is substantially free of a carbon coating, and is formed by thermal reaction of titanium acetoacetonate in a sealed reactor at a temperature of about 700° C. under an autogenically generated pressure of up to about 150 pounds-per square-inch (psi) to form a nanoparticulate carbon-coated anatase $TiO_2$ powder, and subsequently substantially removing the carbon coating;

the $SnO_2$ nanoparticles have a particle size in the range of about 10 to about 20 nm; and the $TiO_2$ nanoparticles have a particle size in the range of about 10 to about 30 nm.

2. A photocatalyst for conversion of carbon dioxide and water into a hydrocarbon and oxygen, the photocatalyst comprising nanoparticles of carbon-doped anatase $TiO_2$ that are substantially free of a carbon coating, and nanoparticles of rutile $SnO_2$ that are substantially free of a carbon coating.

3. The photocatalyst of claim 2, wherein the nanoparticles of $SnO_2$ have a particle size in the range of about 10 to about 20 nm, and the nanoparticles of $TiO_2$ have a particle size in the range of about 10 to about 30 nm.

* * * * *

UNITED STATES PATENT AND TRADEMARK OFFICE
CERTIFICATE OF CORRECTION

PATENT NO. : 9,314,770 B2
APPLICATION NO. : 13/247759
DATED : April 19, 2016
INVENTOR(S) : Ingram et al.

Page 1 of 1

It is certified that error appears in the above-identified patent and that said Letters Patent is hereby corrected as shown below:

IN THE CLAIMS

Column 10, claim 1, line 59, delete "on" and insert --ion--.

Signed and Sealed this
Fifth Day of July, 2016

Michelle K. Lee
*Director of the United States Patent and Trademark Office*